United States Patent [19]

Von Sutfin

[11] Patent Number: 5,188,531
[45] Date of Patent: Feb. 23, 1993

[54] METHOD AND EQUIPMENT FOR TREATMENT OF PERIODONTAL DISEASE

[76] Inventor: Lloyd Von Sutfin, R.R. #2, Box 63C, Norwich, Vt. 05055

[21] Appl. No.: 863,342

[22] Filed: Apr. 1, 1992

Related U.S. Application Data

[63] Continuation of Ser. No. 91,969, Sep. 2, 1987, abandoned, which is a continuation-in-part of Ser. No. 906,242, Sep. 12, 1986, abandoned.

[51] Int. Cl.$^5$ .......................... A61C 1/07; A61C 3/03; A61C 3/00; A61C 5/00
[52] U.S. Cl. .................................. 433/188; 433/141; 433/215; 433/119
[58] Field of Search .................. 433/72, 75, 51, 81, 433/86, 118, 119, 136, 141, 159, 215, 229

[56] References Cited

U.S. PATENT DOCUMENTS

| | | | |
|---|---|---|---|
| 575,750 | 1/1897 | Winkler | 433/143 |
| 1,586,302 | 5/1926 | Funk | 433/141 |
| 3,058,225 | 10/1962 | Ward | 33/172 E |
| 3,091,033 | 5/1963 | Ellman | 433/86 |
| 3,526,219 | 9/1970 | Balamuth | 433/119 |
| 3,584,112 | 6/1971 | Morris et al. | 424/7.1 |
| 3,645,255 | 2/1972 | Robinson | 128/66 |
| 3,753,434 | 8/1973 | Pike et al. | 433/32 |
| 3,924,335 | 12/1975 | Balamuth et al. | 433/119 |
| 3,956,826 | 5/1976 | Perdreaux, Jr. | 433/86 |
| 4,169,984 | 10/1979 | Parisi | 433/86 |
| 4,283,174 | 8/1981 | Sertich | 433/119 |
| 4,364,730 | 12/1982 | Axelsson | 433/141 |
| 4,592,728 | 6/1986 | Davis | 433/81 |
| 4,681,544 | 7/1987 | Anthony | 433/215 |
| 4,685,883 | 8/1987 | Jernberg | 433/215 |
| 4,695,255 | 9/1987 | Overmyer | 433/215 |
| 4,731,019 | 3/1988 | Martin | 433/119 |
| 4,804,364 | 2/1989 | Dieras et al. | 433/119 |
| 4,818,230 | 4/1989 | Myers et al. | 433/215 |

FOREIGN PATENT DOCUMENTS

| | | | |
|---|---|---|---|
| 0002904 | 7/1979 | European Pat. Off. | 433/141 |
| 2566262 | 12/1985 | France | 433/119 |

OTHER PUBLICATIONS

Dentsply/Cavitron Model 2001, Instruction Manual, pp. 1-15.
MEDIDENTA International, Inc. "New Wave in Endodontics-Sonic Air MM3000 Sonic Air Endo System".

*Primary Examiner*—Gene Mancene
*Assistant Examiner*—Nicholas D. Lucchesi
*Attorney, Agent, or Firm*—Sughrue, Mion, Zinn, Macpeak & Seas

[57] ABSTRACT

The present method and apparatus are directed to the treatment of periodontal disease. A contoured, calibrated instrument is employed to probe the gum tooth interface to locate periodontal lesions containing bacteria and their by-products such as plaque, calculus, and diseased tissue. After the prove has identified a periodontal lesion, a vibrating instrument having a configuration similar to the probe is inserted into the periodontal pocket in a manner so as to perferentially contact the tooth. The frequency and power used to drive the vibrating instrument is adjusted to a level sufficient to cauese the instrument to fracture the cementum and cause the instrument to fracture the dentin of the tooth leaving the dentinal tubuli exposed. The lesion is irrigated during treatment with a vibrating instrument with solution having preferably a pH between about 5 and 5.5. The lesion is closed by applying pressure for a time sufficient to assure the fibrin network penetrates the dentinal tubuli thus assuring that the periodontal tissue reattaches to the tooth.

35 Claims, 3 Drawing Sheets

METHOD AND EQUIPMENT FOR TREATMENT OF PERIODONTAL DISEASE

This is a continuation of Application Ser. No. 07/091,969, filed Sep. 2, 1987, now abandoned, which is a continuation-in-part of Application Ser. No. 06/906,242, filed Sep. 12, 1986 now abandoned.

FIELD OF INVENTION

The present invention is directed to the treatment of periodontal disease regeneration of periodontal tissues and to the instruments employed for such treatment.

BACKGROUND ART

Periodontal disease is an infection of the root surface of the tooth and the principal cause of adult tooth loss. The inflammatory response adversely affects the surrounding gum and bone tissue and the bacteria may invade these tissues. Periodontal disease can have both local and systemic consequences ranging from sore gums to death. Periodontal disease is currently treated by both medication and surgery. A number of patents are directed to methods and equipment for the treatment of periodontal disease.

U.S. Pat. No. 1,622,616 of Olives Temple, entitled DEVICE FOR APPLYING OINTMENT TO THE GUMS, teaches a device for applying ointment to the inner and outer surfaces of the gums for the treatment of diseases such as pyorrhea The device of the '616 patent has V-shaped arms to which are attached absorbent pads and an ointment applicator. The device both applies ointment to the gums and massages the gums.

U.S. Pat. No. 1,691,785 of Obrin Remensnyder, entitled DENTAL MASSAGE DEVICE, teaches a device for treating diseases, such as pyorrhea, and for exercising and massaging the gums. The device has a compressible elastic base pad which extends up to and contacts the free margin of the gum tissue.

More recent developments in the treatment of periodontal disease have been in the area of diagnostic equipment. U.S. Pat. No. 3,943,914 of James W. Grenfell, Fred M. Sorenson, Hiroshi Ueno, Masato Miyahara, entitled REMOTE-RECORDING PERIODONTAL DEPTH PROBE, teaches an apparatus for the measurement and remote recording of the depth of the gingival sulci and similar anatomical recesses. The apparatus has a depth probe which is ensheathed in a slidable tubular sleeve. The probe is electrically connected to a transducer which can produce a visual record of the sulcus depth at various locations.

U.S. Pat. No. 4,058,115 of Friedrich M. 0. Forster, entitled METHOD AND APPARATUS FOR EXAMINING HUMAN PERIODONAL TISSUES, teaches a method for examining periodontal tissues. The method of the '115 patent requires that force be exerted on the tooth by a rigid medium which slides in a transducer head. The movement of the tooth responsive to the force is measured.

U.S. Pat. No. 4,182,312 of David R. Mushabac, entitled DENTAL PROBE, teaches a dental probe which has a stylus connected through a rod to a three position transducer. Signals are produced indicating the position of the probe. Contact between the tip of the stylus and the patient's tissue completes a circuit which turns on a recording mechanism which receives and records the outputs of the transducers.

U.S. Pat. No. 4,203,223 of Eugene P. Lautenschlager, Peter J. Robinson and Randall M. Vitek, entitled PERIODONTAL PROBE, teaches a force-controlled periodontal probe, having a scale-marked shaft which is covered by a sliding alignment sleeve. Measurements of gingival sulcus depths are made when force is applied to the handle of the instrument. The resistance of the probe to further penetration by the tip portion of the shaft causes the shaft to shift which, in turn, produces displacement.

U.S. Pat. No. 4,250,895 of Sidney Lees, entitled PERIODONTAL PROBE, teaches a periodontal probe for use with a hydraulic pressure system. The probe monitors the flow of gas from the tip to determine the depth of a periodontal pocket.

U.S. Pat. No. 4,340,069 of Ronald N. Yeaple, entitled FORCE-SENSITIVE PROBE AND METHOD OF USE, teaches a method and the mechanical and electronic apparatus for examining a periodontal pocket. The probe of the '069 patent has a moveable lever and a probe tip. The probe tip is inserted into a periodontal pocket and the movement of the tip within the probe body is measured.

U.S. Pat. No. 4,445,857 of Arnoldus J. Borst, entitled DENTAL CAVITY MEASURING INSTRUMENT, teaches an instrument for measuring the depth of a periodontal pocket.

U.S. Pat. No. 4,485,823 of Akiya Yamaguchi, Marvin M. Stark and Kenneth B. Soelberg, entitled APPARATUS FOR DIAGNOSING ENVIRONMENTAL TISSUE OF TOOTH, teaches an apparatus for diagnosing the environmental tissue of teeth to identify the health of the peripheral tissue. The apparatus of the '823 patent senses the frequency band or amplitude of mechanical oscillation transmitted through the tissue.

Current treatment of periodontal disease requires removal of all causative bacterial factors and diseased soft tissue.

In one prior art method, called gingivectomy, the diseased soft tissue (or gum tissue) and also all the health gum tissue is first surgically removed, and then the exposed root is scraped until a smooth root surface is obtained.

Another method known as flap surgery has several variations. Essentially the gum tissue is cut or incised to free the gum from the teeth, the interconnection of the gum between the teeth and the bone. The gum tissue is sliced; folded or deflected away from the tooth; soft tissue, diseased or not, remaining between and around the teeth is removed with knives or by scraping, and then the causative factors are removed by scraping the root of the tooth until the root is smooth. After the root has been scraped, the gum folds or flaps are replaced against the exposed bone and tooth and sutured together. Bone reshaping may also be done. In all methods in which the tooth is scraped a smear layer is formed on the tooth. This smear layer interferes with healing and regeneration.

After the root has been treated by one of the prior art methods such as discussed above a packing is placed over the exposed root area and associated gum tissue.

Substances can be applied to the root surface after mechanical treatment of the root. Citric acid solutions are sometimes used for this purpose. When substances are applied to the root surface additional time and possibly further separation of the gum tissue may be required.

The nature of the gingivectomy and flap surgery procedures are such that areas of the gum much greater in extent than the areas involved with the periodontal disease are involved by the surgical procedure. Additionally these procedures cause a loss of supporting attachment of the gum and bone to the tooth. This can limit the number of times the procedures can be repeated if the disease recurs.

An alternate, but difficult method called root planning or curettage leaves the gum in place. With the gum in place a hand instrument is used to scrape the root of the tooth until the smoothness of the root indicates that the root is free of causative factors. During the procedure adjacent gum tissue may also be removed using the same instrument used to scrape the root of the tooth. Often because of the rigor required to accomplish the removal of causative agents gum tissue may be separated. The separated gum tissue must be sutured. A packing is frequently used for mechanical protection.

These prior art procedures are overly invasive, time consuming and painful. In addition, the incisions and sutures are potential infection sites. Further, since the packing promotes bacterial growth and may interfere with attachment of the gum to the tooth, the healing process is prolonged and may require several weeks. Additional minor procedures in which the sutures and packing must be removed are also required. During the time of healing and for a period of several weeks thereafter the patient must be monitored to assure that healing is progressing and the treated areas remain infection free.

SUMMARY OF THE INVENTION

It is an object of the present invention to treat periodontal disease while minimizing invasive surgery.

It is an object of the invention to reduce the number of procedures and appointments required for the treatment of periodontal disease.

It is a further object of the present invention to minimize the change in the appearance in the teeth and gums.

It is an object of the present invention to encourage regeneration of periodontal tissues. It is an object of the present invention to rapidly destroy the infecting bacteria within the periodontal lesion.

It is an object of the invention to bring the disease in a given mouth under control rapidly so that areas treated earlier will be less likely to become reinfected from areas not yet treated.

It is an object of the present invention to provide with the same method different procedure or levels of treatment which may differ depending on the periodontal disease.

It is an object of the present invention to reduce the probability of infection following the treatment of periodontal disease. IT is an object of the present invention to perform the different levels of treatment form within the periodontal lesion itself. It is an object of the present invention to accomplish the different levels of the treatment without creating any exposed raw surfaces of gum tissue or bone. It is an object of the present invention to promote rapid regeneration and attachment of gum tissue and bone to the root of the tooth.

It is another object of the invention to provide a method for treatment of periodontal disease which avoids the use of sutures.

Still another object of the invention is to provide a method for treating periodontal disease which does not require packing of the gums and teeth. It is still another object of the invention to promote rapid and thorough healing of periodontal lesions.

Yet a further object of the present invention is to provide a method of treating periodontal disease which leaves the gum tissue in place.

These and other objects of the present invention will become apparent from the following description and figures.

The present invention employs a contoured calibrated probe which is moved along the gum-tooth junction to locate periodontal lesions. The periodontal lesions contain the infecting bacteria and their by-products such as plaque, calculus, biochemical irritants and diseased, inflamed tissue. The infecting bacteria are not just on the surface of the tooth but are within the tooth structure itself. Lesions may be located with the probe prior to treatment and plotted graphically. Alternatively, when a lesion is located it may be treated.

For treatment an instrument herein called, a dental instrument having a configuration similar to the configuration of the contoured probe is inserted into the lesion and placed in contact with the diseased tissues. The dental instrument is used to fractionate diseased soft tissue and hard tissue and bacteria; and to debride disease affected regions of the supporting bone and open up the bone tissue for regeneration. The dental instrument must be driven with sufficient vibrating energy to dislodge, clean, and fracture remove calculus and plaque from the surface of the tooth and to disintegrate bacteria within the lesion. It is preferred that the instrument use mechanical energy generated at ultrasonic frequency. Removal of the calculus and plaque exposes the cementum which covers the root of the tooth.

After the calculus and plaque have been removed, the diseased cementum and dentin are removed from the tooth. The energy requirement for the removal of the diseased cementum and dentin is higher than the energy required for the removal of calculus and plaque and is high enough to allow selected removal of healthy soft tissue and bone.

If probing after the initial treatment indicates that a portion of the surface of the root is still rough, or soft and tacky, then insertion of the instrument may be repeated until a hard, granular root surface is obtained. If the root surface is tacky, the probe will stick to the surface in the manner in which a probe would stick to taffy. Healthy dentin has a hard granular surface and thus can be readily identified by the probe. A hard granular surface will respond to the probe in a manner similar to the response of the probe to the surface of a polished acrylic uniformly abraded with a machinists crocus cloth and then lubricated with mineral oil.

A fluid is used to cool and lubricate the instrument. In addition, the fluid irrigates the lesions transmits energy throughout the lesion, promotes exposure of the organic phase of dentin and cementum, and stabilizes the initial stages of the healing and the regeneration process. The fluid aids the dislodging and fracturing of calculus, plaque bacteria and diseased soft and hard tissue. The fluid should promote the removal of, or prevent formation of, a smear layer on the root surface. The solution should be mildly decalcifying. A solution having a pH between about 5 and 5.5 is preferred to enhance the exposure of dentinal tubuli and the organic phase of the root of the tooth.

After the hard granular surface of the tooth has been obtained, and properly prepared and adequate soft tissue has been disintegrated and bone structure prepared, the sharp curette should be inserted into the lesion to detock from the soft tissue any remaining diseased and/or disintegrated soft tissue, remove fractured cementum plaque, calculus, and bacteria and/or bacterial debris. If necessary or desired the tip of curved scissors can be inserted into the now enlarge lesion to cut away unwanted soft tissue from the inside of the gum tissue.

It is preferred that there be a time interval between the preparation of the root surface and debridement with the curette. The time interval allows for blood clot formation the fibrin network of the clot will form on and around microscopic on the foreign debris and bacteria, and thus makes the debris and bacteria more readily removable by removing the clotted blood. This time interval is typically about two to five minutes. When several teeth are being treated in sequence, the duration of each step of the procedure can be adjusted to create the desired time interval between the root surface preparation and insertion of the curette.

Care should be taken to minimize cutting and scraping contact between the curette and the freshly exposed root surface since smearing of the dentin or cementum over the dential tubuli and exposed organic phase should be avoided. Cutting a tooth with a metal instrument drags surface material and creates a smeared surface. Thus, it is recommended that contact be regulated by directing the force of the curette tip or edge against the soft tissue or bone. Should the above inadvertently occur the vibrating energy can be reapplied with very light pressure to assure the absence of a smear layer on the tooth root.

After treatment, the lesions are then closed by strong pressure. The pressure should be of such magnitude and maintained for a time sufficient to assure that the fibrin network of the blood clots link to the dentinal tubuli and organic components, and that the fibrin network is of minimum thickness from the deepest part of the lesion, i.e., where the tooth-periodontal ligament-bone meet. The pressure promotes the healing process in which the tissue attaches to the root. Substances such as Tissucol ® or Tissuseel ®, which contain fibronectin, stabilize and promote clotting and healing may be introduced into the lesion after debridement and before pressure to reduce the time for clotting, strengthen the clot, and aid in attachment of the connective tissue to the root. Tetracycline solutions can also be used in this regard. Lesions from which large volumes of tissues have been removed may be filled with a porous material, such as a collagen sponge, to aid in stabilizing the fibrin network of the clots which attach the periodontal tissue to the root. A membranous material may be inserted between gum and tooth and bone and fastened in any suitable way to impede the ingrowth of epithelium between the surgically exposed connective tissue and the tooth to allow increased time for connective tissue components to regenerate from the deepest part of the lesion, i.e., where the tooth-periodontal ligament-bone meet.

BEST MODE OF CARRYING THE INVENTION INTO PRACTICE

The present invention is directed to the treatment of periodontal disease regeneration of periodontal tissues and to the instruments employed for such treatment.

To practice the present method, a contoured, calibrated probe is moved along the gum-tooth interface to locate periodontal lesions. These lesions contain bacteria and their by-products such as plaque, calculus, and diseased hard and soft tissue.

Figure 1:
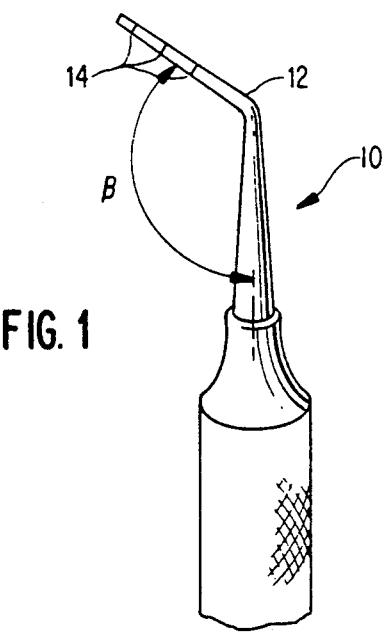
FIG. 1 is a perspective view showing of the contours of the calibrated probe used in accordance with the present invention to locate lesions.

FIG. 1 illustrates a contoured, calibrated probe 10 used to locate the periodontal lesions in accordance with the present method. The probe 10 has a long extended prong 12 of circular cross section. The prong 12 has index marks 14 which allow for indexing the depth of periodontal lesions. The prong 12 is resilient and allows the user to sense the character of the surface of the tooth. When the probe 10 is used to examine the upper gums, the probe 10 should have an included angle $\beta$ of between about 128° and 130°. When the probe 10 is used to examine the lower gums, the probe should preferably have an included obtuse angle $\beta$ of about 119° and 121°.

Figure 2:
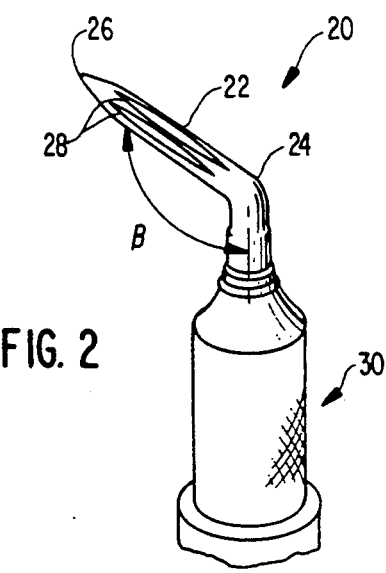
FIG. 2 is a perspective view showing the tip of a vibrating instrument used to practice the present invention.

When a lesion is located, a dental instrument 20, such as shown in FIG. 2, suitable for transmitting disintegrating energy to the tissues is inserted into the lesion. An included angle $\beta$ is formed between the prong 22 and shank 24 of the dental instrument 20. The angle should preferably be the same as the angle of the probe used to locate the lesion.

Having the dental instrument 20 with the same configuration as the calibrated probe 10 provides the user a reference with respect to anatomical landmarks and the kinesthesia of the user's hand which allows for indexing the position of the instrument with respect to the lesion located by the calibrated probe 10. The preferred angles are important in reducing operator fatigue and increasing access, however, in special situations customized angles may be utilized.

Figure 3:
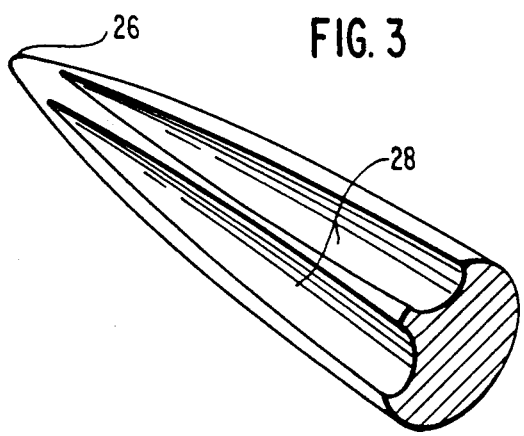
FIG. 3 is an enlarged perspective view of the tip of the vibrating instrument show in FIG. 2.

The dental instrument 20 has a rounded cross sectional configuration as illustrated in FIG. 3. The prong 22 of the dental instrument 20 has a blunt pointed tip 26 and two channels 28 for conducting coolant along the prong 22 from the coolant tube 30.

Figure 4:
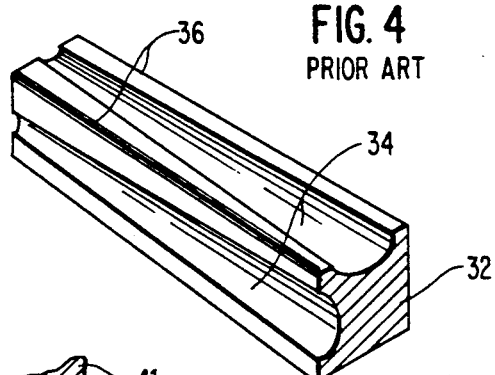
FIG. 4 is a perspective view showing the tip of a prior art vibrating instrument.

The dental instrument 20 differs from prior art instruments such as the Dentsply TF1-EWPP (Perio-Probe)

shown in FIG. 4. The prior art instrument has a rectangular cross-section 32 with a pair of channels 34 to permit the flow of a coolant. The prior art instruments employed sharp edges 36 to scrape the tooth root and remove diseased root tissue, while the instrument 20 of the present invention removes the tissue by imparting sufficient energy to the tissue to cause it to fracture and cleave or disintegrate is omnidirectionally effective.

Only the smooth sides of the dental instrument and root the beginning of curvature of the tip are used for debridement.

The point of the tip is not used against or directed into the tooth structure. It is blunt and even at high energy levels under normal light paint brush type pressures will not penetrate healthy soft connective tissue. When firm resistance to the advancement of the tip along the tooth-soft tissue interface or through the soft tissue has been reached debridement should not be extended further. However, if for purposes of final adaptation a discrete or limited amount of separation of and/or removal of healthy soft tissue is desirable, pressing the pointed tip within the lesion into the healthy tissue in the desired direction will cause separation insert. This additional step is an optional supplement to tooth root debridement and preparation and allows for internal reshaping of gum tissues.

The instrument 20 is driven by a dental power source capable of providing sufficient energy to remove calculus, plaque, cementum and dentin. When, for example, a Cavitron ® Powermatic ® is used, the recommended power setting, which is sufficient to remove calculus and plaque is the medium power setting. After the plaque and calculus are removed from the tooth, the power setting should be set at high or maximum to cause the instrument to fracture and cleave the diseased cementum and diseased dentin from the tooth and disintegrate bacteria in and on the tooth as well as soft tissue. The prior art uses a lower energy input since the prior art method teaches removing calculus and plaque but not dislodging tooth structure or disintegrating bacteria or removing gum or bone tissue.

Figure 5:
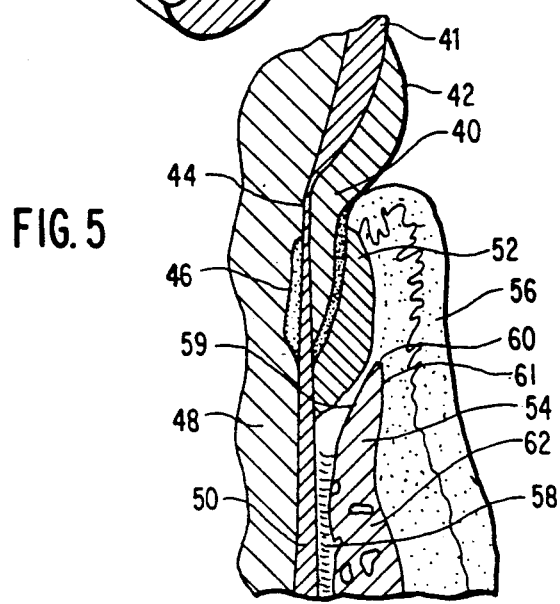
FIG. 5 is a cross sectional view of a periodontal lesion.

The dental instrument 20 is placed in a periodontal lesion shown in FIG. 5. The dental instrument should be directed as quickly as possible to the deepest part of the lesion. Much of the more superficial calculus, plaque will be removed in passing as the deeper portion of the lesion is treated. Initially, the instrument 20 dislodges the plaque and calculus 42 contained in the periodontal lesion 40. After the plaque and calculus have been dislodged and removed, the diseased cementum 44 and dentin 46 on the tooth root will be dislodged and bacteria disintegrated. Removing the diseased cementum 44 and dentin 46 leaves the healthy dentin 48 exposed. Preferably treatment is carried out from the deepest portion of the lesion to the more superficial portion until all diseased surfaces have been treated.

The exposed healthy dentin 48 provides a hard granular surface. The healthy dentin 48 and cementum 50 can be readily identified using a probe. The hard granular surface is a surface over which the probe 10 will readily slide. It will have a roughness that can be felt as if the probe 10 is contacting a surface of polished acrylic uniformly abraded with machinists crocus cloth then lubricated with mineral oil. The diseased surface cementum 44 and dentin 46 will be tacky and provide resistance to the probe 10 or it may feel rough and hard. Often the surface will seem to increase in roughness to the probe 10 and then become smooth, hard and granular.

The dental instrument 20 shown in FIG. 2 can be used to fractionate soft tissue 52 and as well as to debride diseased affected supporting bone 54 shown in FIG. 5. The soft tissue 52 and disease supporting bone 54 is fractionated by applying the tip the soft tissue 26 of the dental instrument 20 to the diseased tissue and bone. The curvature of the tip 26 of the instrument 20 is such as to avoid easy penetration of the healthy gum tissue 56 or the periodontal ligament 58 at light pressure but great enough to allow penetration if such is desired. Preferably the radius of curvature of the tip is between about 0.004 and about 0.020 inches.

The curvature and taper of the tip also allows insertion and treatment of very narrow spaces between teeth and between angular bone defects and the tooth.

During treatment with the dental instrument, the lesion 40 is irrigated with the fluid used to cool the instrument and optimize the transmission of energy inside the lesion 20. The fluid is removed from the mouth by high volume air flow suction. To minimize smearing of the exposed dentin 48 and to enhance the exposure of dentinal tubuli and the organic phase of the dentin 48, a solution having a pH between about 5 and 5.5 is preferred.

The use of the dental instrument 20 within a periodontal lesion with the gum in place provides an advantage over the open surgical procedures since the instrument so positioned can remove both soft and hard diseased tissue in a single step. Furthermore, the gum tissue wall directs the movement of the dental instrument 20 and assists in concentrating the instrument's energy into the soft tissue bacteria root structure and bone, thus promoting disintegration and fracture. The lesion also serves as a reservoir for the coolant and thus aids in the etching of the root surface and transmitting energy to the entities being disintegrated.

If after initial treatment with the dental instrument, further probing indicates that the regions of the root are still roughened, irregular, or soft and tacky, the vibrating instrument can be reinserted and the treatment can be repeated on these areas.

Figure 6:
FIG. 6 is a side view of a curette which is used to remove the residual by-products and excess soft tissue which remain after treatment of the tooth in accordance with the present invention.
Figure 7:
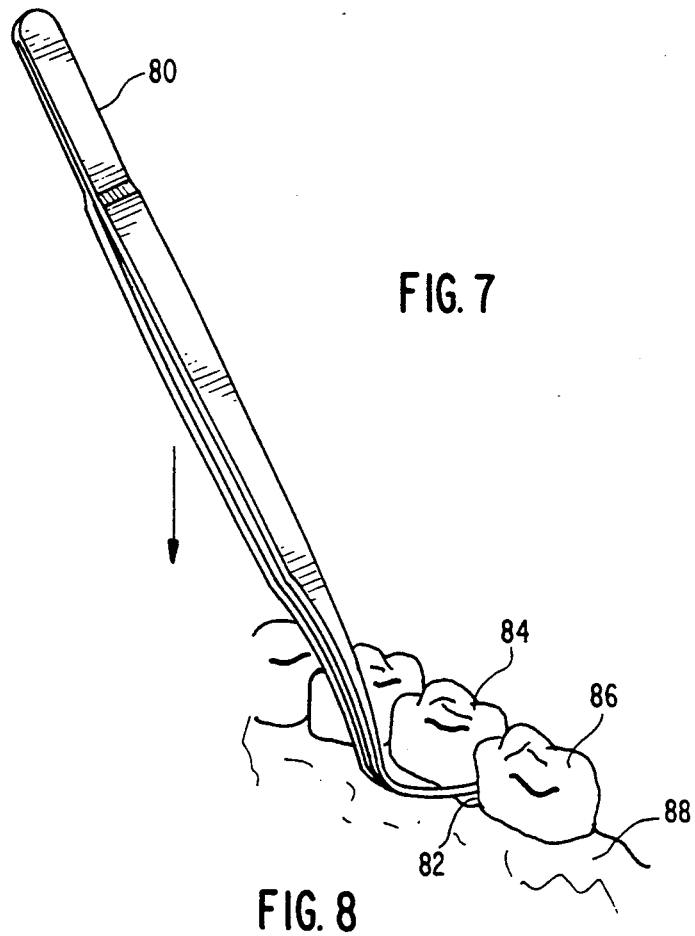
FIG. 7 is a perspective view of the use of dental pliers to apply pressure to the gum tissue in order to adapt the gum closely to the root and bone and promote attachment of the periodontal tissues to the root of the tooth.

After the surface of the tooth and other tissues are prepared as repaired, a sharp currette 70, shown in FIG. 6, is inserted into the lesion 40, as shown in FIG. 5, to remove any remaining diseased soft tissue, fractured cementum and the associated plaque and calculus and other debris dislodged during previous steps of the treatment. The sharp edge 68 of the curette 70 is used to cut away any residual unwanted soft tissue 52 attached to healthy periodontal tissue 56. The curette is also used to scrape the supporting bone 60 and 62.

It is preferred that a time interval of about two to five minutes occur between the preparation of the tooth and the insertion of the curette. It is preferable to minimize suctioning of the lesions directly during this time interval and this allows for clot formation on the debris and bacteria. These can then be readily removed with the clots. At this point suctioning with a conical tip can be used to aid in the removal of debris laden clots.

Care should be taken to minimize contact between the curette and the freshly exposed dentin 48 to avoid smearing of the dentin over the dentinal tubuli and exposed organic components. When debridement is completed and large external blood clots have been cleared away, preferably with gauze and not with suction so that the clot will remove in the lesion, the gum will usually surround the teeth in a loose fitting way in the regions where treatment has been concentrated or carried out. The gums will be unchanged in areas where no periodontal lesions existed and treatment was not carried out. Usually the interdental connections of the gum from the outerside of the jaw to the innerside of the jaw will remain intact. The result is a loose fitting, connected envelope flap of very discrete proportions and modulated in extent by preventing pathological conditions. There is no or little raw surface. Application of firm pressure this modulated connected envelope flap will collapse and plastic deform to adapt to the tooth and underlying bone.

After the treated lesion 40 is cleaned with the curette 70, the lesion is closed by strong pressure which is maintained for a time sufficient to express fluid from the clot and assure the fibrin network of the blood clot links to the dentinal tubuli and the organic components. Pressure can be applied to the gum with a pliers 80. The pliers 80 is inserted into the region 82 between teeth 84 and 86 and pressure is applied to the gum 88 for about 3 to 4 seconds. A small amount of gauze between the pliers and the gum helps to evenly distribute the pressure, reduce injury and soak up fluid from the condensing clot. The pliers 80 are removed and light pressure produced by a gauze compress maintained for 0.5 to 1 hour can be used to promote attachment.

Lesions with large volume and from which a large volume of tissue has been removed may be packed with a bio-compatible material 90, such as a collagen sponge, which will stabilize the fibrin clot. The gum is pulled aside and an appropriately shaped sheet or block of sponge is inserted with fine pliers and/or the contoured probe. The gum is allowed to spring back and moderate pressure with a gauze compress is applied.

While it is desireable that the gum initially attaches to a portion of the root surface that has been prepared, it is not absolutely necessary because the attachment will continue to grow crownward, known as "creeping reattachment," thus attaching to some of the area where the periodontal tissue had recessed away from the tooth but to which direct linking of fibrin and subsequent regeneration of periodontal tissue did not occur immediately.

The surgical injury created is very circumscribed and the hard granular textured surface of the root offers a receptive surface for tissue attachment. These aid in the rapid healing of the lesion. Fibrin clot formation and attachment to a hard granular surface and the periodontial tissue occurs rapidly and thus, the necessity to suture and pack the gums to maintain pressure for extended periods of time is eliminated. Also because the surgical injury is so circumscribed by the present method, no or little raw surface is exposed and the necessity to pack the gums for mechanical protection is eliminated. Thus packing and suturing are obviated by the present method.

Figure 8:
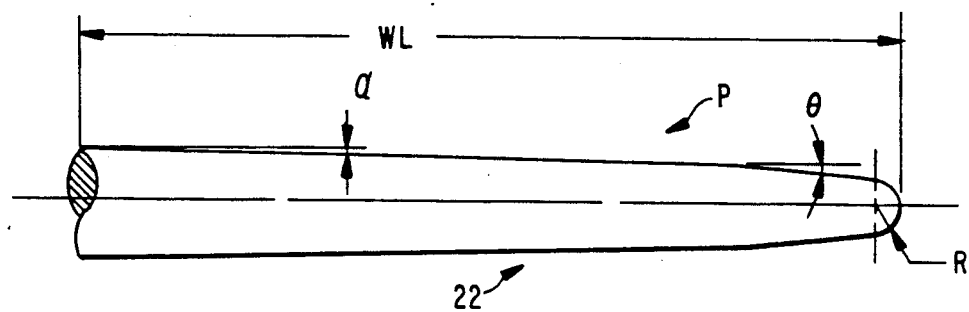
FIG. 8 shows diagramatically an enlarged side elevational view of the preferred vibrating prong of the present invention.
Figure 9:
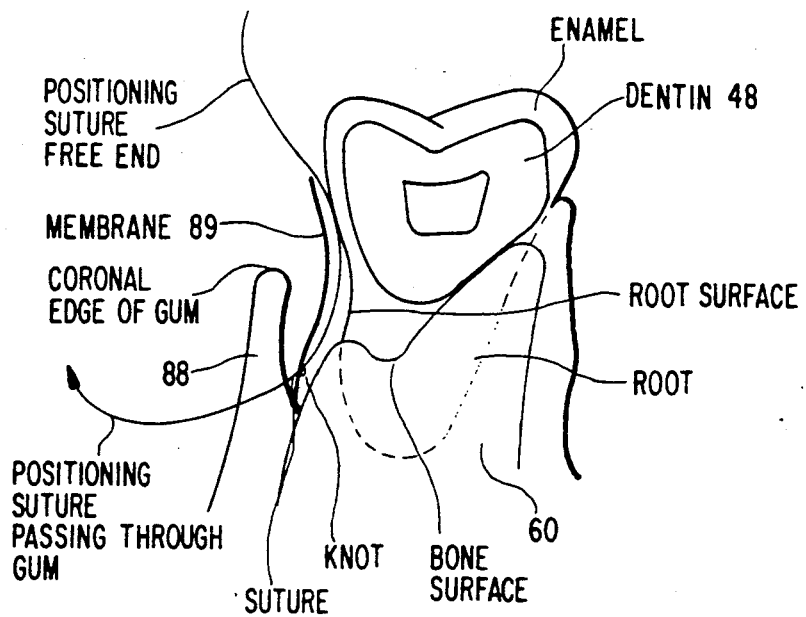
FIG. 9 is a sectional view showing a lesion packed with a bio-compatible material membrane.
Figure 10:
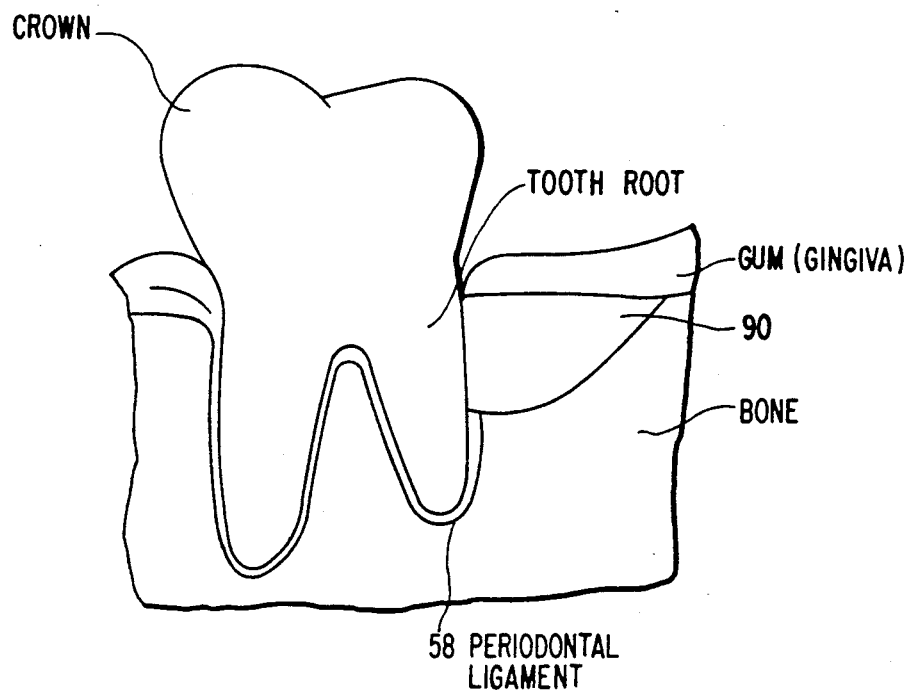
FIG. 10 is a sectional view showing a lesion packed with a porous, bio-compatible material pad.

Turning now to FIG. 8, the preferred working length (WL) of the prong 22 is between 5/16 and ½ of an inch. The diameter of the prong 22, at one end of its working length, is approximately 0.040 inches and this diameter can range from about 0.035 to 0.065 inches. The prong has a conical taper over its length which continues until it gradually transforms into the hemi-spherical blunt pointed tip 26. The blunt pointed tip 26 has a radius R generally between 0.007 and 0.011 inches. Preferably, the prong 22 has two tapered sections, the first taper being of approximately 2 degrees and the second taper $\theta$ being of approximately 4 degrees and the change between the tapers occurring at point P a distance of approximately 1/16 of an inch away from the blunt pointed tip 26. It is important to note that the utilized tapers of the prong are dependent upon the diameter of blunt pointed tip and the working length of the prong.

Since the prior art devices typically have rectangular shaped cross-section tips approximately a 40 percent reduction in the diagonal width or diameter of the of the prong is achieved by the present invention. The blunt pointed tip and second taper further increases the fineness of the prong. This enables present prong to be inserted into significantly smaller areas between the teeth and between bone and teeth. Furthermore, since the prong and tip are generally rounded in shape, virtually any surface area of the prong may be effectively and safely used to impart omnidirectionally vibrational energy to the tissue unlike the prior art devices which required a defined orientation of the instrument in relation to the tissues, especially tooth and bone.

The tapers and radiused portion of the prong perform different functions in a typical application. The 4 degree tapered conical surface is the primary working surface which contacts the tissue surface and transmits the vibrational energy into it. The 2 degree tapered conical surface is a secondary working surface, e.g., while the 4 degree surface contacts the tooth root the 2 degree tapered conical surface may transmit energy to the opposing soft tissue surface in a more superficial portion of the lesion. Increasing the efficiency of the treatment. The combination of the radiused tip and the first portion of the 4 degree tapered cone form a penetrating surface which can be used to dissect soft tissue from hard tissue, penetrate bone to stimulate regeneration and penetrate soft tissue as a first step in its disintegration in the removal of excess amounts of soft tissue.

In order to further illustrate the method of the present invention the following example is offered.

EXAMPLE

The regions where periodontal lesions exist are identified. This may be done at a pre-treatment visit and the location of such lesions may be mapped for future reference. When treatment is undertaken an area where a periodontal pocket exists is selected. The gum and teeth in the area to be treated are anesthetized with an injection with local anesthetic, such as Carbocaine ™. The upper jaw and gum area will be almost instantly anesthetized, while the lower jaw and gum will take five to ten minutes to be anesthetized.

When treating periodontal disease it is preferred that an antibiotic be given to reduce the chance of infection, and in particular, tetracycline (generic) and derivative antibiotics are preferred as the antibiotic since tetracycline and related antibiotics are effective against the bacteria which cause periodontal infection, segregate preferentially to the tissue adjacent to the tooth, and are felt to promote healing of the gum-bone-tooth interface.

During the treatment, the patient is placed in a prone position with the head free to both tilt and rotate.

The lesion is first previewed with a probe to to identify specific regions needing treatment. The first insertion with the vibrating instrument 20 will explore and transmit energy to the total lesion and frequently lesions affecting several teeth to be treated as a group. Light pressure is applied to move the instrument in the lesion. The pressure is applied with a stroking motion similar to using a paintbrush. There will be distinct resistance to the movement of the instrument which is intermittent and variable (e.g. like the feeling of a rolling pin going over crackers to produce cracker crumbs). Light pressure and the stroking motion is continued over the area of the teeth which, are to be treated until resistance to motion ceases (e.g., all cracker crumbs are nearly uniform in size and uniformly distributed)

The instrument is removed and the area re-examined with the probe. The probe will allow the user to identify areas which are still rough, or soft and tacky and which need additional treatment. The instrument is then reinserted with the same spatial position as the probe and energy is applied at light pressure to the regions of the teeth which require additional preparation. After these regions have been treated, the instrument is removed and the probe is reinserted for a third inspection to isolate any remaining region which will require additional preparation. This is repeated until the root surface feels uniform in texture, hardness and graininess, to the probe 10.

Where the periodontal lesion extends deep to the bone, this creates a bony defect 59 as shown in FIG. 5. When these are encountered, it is preferred that the vibrating instrument 20 be used to disintegrate all tissue contained within the bony defect 59. Additionally, the blunt pointed tip 26 of the vibrating instrument is used to dissect or release the gum tissue from the bone at the crest 60 and 0.039 to 0.078 inches over the crest region 61. The soft tissue, including the periostium, at and over the crest region 61 is disintegrated.

A sharp curette 70 is used to remove the loosened tissue from the bony defect 59 and from the bone surface including the crest 60 and the over the crest region 61. This opens up passages to the marrow spaces and endostial lining, thus promoting regeneration of bone into the space of the lesion. Should excess soft tissue be present it may be reduced by disintegrating this soft tissue from within the lesion beneath the surface leaving the surface intact and uninjured. When treating a quadrant of the mouth (six to eight teeth), the preparation time is in the neighborhood of twenty to thirty minutes for high energy removal of all of the diseased tissue, five to ten minutes for debris and excess soft tissue removal, and five to ten minutes for pressure and gauze compress placement.

After the root surface is and bone are prepared and soft tissue reshaping is complete. A time interval of two to five minutes is allowed before debridement with a curette and/or scissors is started to remove the residual materials. This time allows for clots, which can be easily removed, to form around debris and microbes. The curette should not be scraped against the freshly created root surface, however, it can be used to cut soft tissues and can scrape the bone tissue. In all cases, care should be taken so as to avoid contact with the freshly prepared root surface.

If it is desired to further increase probability of bone regeneration, a membrane may be inserted into the treated lesion between the gum tissue 56 and the tooth surfaces 41, 44 and between the gum tissue 56 and outer surface of the over the crest region 61. The membrane may be tucked into place between the gum tissue 56 and the over the crest region 61 with the probe 10. The part of the membrane which extends to the crown of the tooth 41 may be secured to the crown of the tooth 41 by tying it to the crown with a filament around the tooth or by gluing it to the tooth with tissue glue such as cyanoacrylate. Optionally, the crownward edge of the membrane may be sutured to the free margin of the gum.

If difficulties prevent accurate placement of the deeper edge of the membrane between the gum tissue 56 and the over the crest region 61, one or more guiding sutures can be inserted through the gum at the desired locations of the deeper edge of the membrane. These sutures are then passed through the deeper edge of the membrane and knotted so that they will not pull through the membrane but will pull the membrane down into the over the crest region 61. Sufficient free suture material should be left so that it can be used to retract the suture once the membrane is positioned properly. The end emerging through the gum tissue is cut, the free end is pulled to remove the knotted end of the suture, and the suture removed from the membrane and lesion entirely. The membrane is left within the lesion during the healing period, typically 6 weeks, and is extracted from the lesion by any suitable means at that time.

Dental pliers are used to apply pressure to the gum by placing the tip of the pliers between the teeth and using the pliers to press the gum against the exposed root surface and bone. Pressure should be applied for about 3 or 4 seconds. After the pressure is applied, gauze can be used to pack the gum area for about 30 minutes to an hour. If spaces between the teeth are large, the gauze can be inserted into these spaces for this period.

After the procedure is completed and time has been allowed for initial healing, a resilient stimulator should be used to stimulate the gum between the teeth. One such rubber stimulator is the Butler Interdental Stimulator. This procedure should begin approximately one week after treatment.

While the novel features of this invention have been described in terms of preferred embodiments and particular applications, it will be appreciated that various omissions and substitutions in form and in detail of the apparatus and method may be made by those skilled in the art without departing from the spirit of the invention.

I claim:

1. In a vibrational dental instrument for the treatment of periodontal disease comprising a prong disposed at an obtuse angle $\beta$ with respect to a shank and adapted to provide sufficient energy to fracture and remove disease affected tissue surrounding a tooth, the improvement comprising said prong being substantially conical in shape and tapering into a blunt pointed tip and said prong having at least one longitudinal channel on an exterior surface thereof for conducting coolant along the surface from a coolant tube in the direction of said blunt pointed tip.

2. In a dental instrument according to claim 1 wherein said prong has a working length between 5/16 and ¼ of a inch.

3. In a dental instrument according to claim 2 wherein said blunt pointed tip has a radius of curvature of between 0.007 and 0.011 inches.

4. In a dental instrument according to claim 3 wherein said prong has a first taper $\alpha$ at an angle of approximately 2 degrees for a portion of its working length remote from the tip and a second taper $\phi$ of approximately 4 degrees near the blunt pointed tip.

5. In a dental instrument according to claim 4 wherein said angle $\beta$ is between 119 and 130 degrees.

6. In an energy-emitting dental instrument for treatment of periodontal disease utilizing the physical effects of vibrating energy comprising a prong disposed at an obtuse angle $\beta$ with respect to a shank and adapted to provide sufficient energy to fracture and remove diseased tissue surrounding a tooth, the improvement comprising said prong having a smooth nonabrasive exterior surface without a sharp edge being substantially conical in shape and tapering into a blunt pointed tip, and wherein said prong has a working length of between 5/16 and ½ of an inch, thereby enhancing regeneration of periodontal tissues.

7. A dental instrument according to claim 6, wherein said blunt pointed tip has a radius of curvature of between 0.007 and 0.011 inches.

8. A dental instrument according to claim 7, wherein said prong has a first taper $\alpha$ at an angle of approximately 2 degrees for a portion of its working length remote from the tip and a second taper $\theta$ of approximately 4 degrees near the blunt pointed tip.

9. A dental instrument according to claim 8, wherein the angle $\beta$ is between 119 and 130 degrees.

10. A method for treatment and control of periodontal disease and regeneration of periodontal tissues with the gum tissue remaining in place and connected between the teeth, comprising the steps of:
   (a) tracing the gum-tooth interface with a contoured probe to locate a periodontal lesion;
   (b) inserting a dental instrument having a smooth nonabrasive exterior surface without a sharp edge into said lesion;
   (c) applying vibrational energy with said dental instrument to remove plaque and calculus contained in said lesion and contacting the tooth;
   (d) contacting diseased cementum and diseased dentin with said dental instrument while applying sufficient vibrational energy to said dental instrument to cause said diseased cementum and said diseased dentin to fracture;
   (e) irrigating the lesion during steps (c) and (d) with a fluid to remove fractured and fragmented plaque, calculus and fractured cementum and dentin;
   (f) removing said dental instrument;
   (g) inserting a sharp curette into said lesion to remove remaining dislodged cementum, calculus and plaque; and
   (h) closing the lesion by applying pressure for a time sufficient to promote attachment of the gum to the tooth; thereby enhancing said regeneration.

11. The method of claim 10 wherein said fluid has a pH of between about 5 and 5.5.

12. The method of claim 10 further comprising reinserting said probe to isolate diseased dentin and calculus before proceeding with step (a), thereafter repeating steps (b) through (f) until reinsertion of said probe confirms all of said diseased cementum and dentin is removed.

13. The method of claim 12 further comprising the step of irrigating the lesion with a fluid containing a blood clotting agent and/or healing promoting agent after step (g).

14. The method of claim 12 wherein after confirmation that all diseased dentin and cementum has been removed a time interval of 2 to 5 minutes is provided before said curette is inserted into said lesion.

15. The method of claim 14 wherein a force is applied to said gum with dental pliers.

16. The method of claim 12 further comprising the step of removing soft tissue from the inside of the lesion with surgical scissors.

17. The method of claim 10 wherein the dental instrument is employed to remove diseased and excess soft tissue from within the lesion.

18. The method of claim 17 wherein said dental instrument is also employed to remove soft tissue from and expose the regenerative bone surfaces in and around the periphery of the lesion.

19. The method of claim 10 wherein an antibiotic is administered to the patient prior to step (a).

20. The method of claim 10 wherein a healing promoting agent is administered.

21. A method for treatment and control of periodontal disease and regeneration of periodontal tissues with the gum tissue remaining in place and connected between the teeth, comprising the steps of:
   (a) tracing the gum-tooth interface with a contoured probe to locate a periodontal lesion:
   (b) inserting a dental instrument into said lesion;
   (c) applying vibrational energy with said dental instrument to remove plaque and calculus contained in said lesion and contacting the tooth;
   (d) contacting diseased cementum, diseased dentin, and diseased soft tissue from bone with said dental instrument while applying sufficient vibrational energy with said dental instrument to cause said diseased cementum and said diseased dentin to fracture, and to remove diseased soft tissue from the bone and expose regenerative bone surfaces in and around the periphery of the lesion;
   (e) irrigating the lesion during steps (c) and (d) with a fluid to remove fractured and fragmented plaque, calculus, fractured cementum and dentin, and diseased soft tissue;
   (f) removing said dental instrument;
   (g) inserting a curette into said lesion to remove remaining dislodged cementum, calculus and plaque; and
   (h) closing the lesion by applying pressure for a time sufficient to promote attachment of the gum to the tooth; and
   (i) placing in the lesion a bio-compatible porous material before the lesion is closed by pressure.

22. A method for treatment and control of periodontal disease and regeneration of periodontal tissues with the gum tissue remaining in place and connected between the teeth, comprising the steps of:
   (a) tracing the gum-tooth interface with a contoured probe to locate a periodontal lesion;
   (b) inserting a dental instrument into said lesion;
   (c) applying vibrational energy with said dental instrument to remove plaque and calculus contained in said lesion and contacting the teeth;
   (d) contacting diseased cementum, diseased dentin, and diseased soft tissue proximate to the bone with said dental instrument while applying sufficient vibrational energy with said dental instrument to cause said diseased cementum and said diseased dentin to fracture;
   (e) irrigating the lesion during steps (c) and (d) with a fluid to remove fractured and fragmented plaque, calculus and fractured cementum and dentin;
   (f) removing said dental instrument;
   (g) inserting a curette into said lesion to remove remaining dislodged cementum, calculus and plaque; and
   (h) closing the lesion by applying pressure for a time sufficient to promote attachment of the gum to the tooth; and (i) wherein the contoured probe and the dental instrument have the same included angle of between 128° and 130° and are used in the treatment of the upper gums.

23. A method for treatment and control of periodontal disease and regeneration of periodontal tissues with the gum tissue remaining in place and connected between the teeth, comprising the steps of:
   (a) tracing the gum-tooth interface with a contoured probe to locate a periodontal lesion;
   (b) inserting a dental instrument into said lesion;
   (c) applying vibrational energy with said dental instrument to remove plaque and calculus contained in said lesion and contacting the tooth;
   (d) contacting diseased cementum and diseased dentin with said dental instrument while applying sufficient vibrational energy with said dental instrument to cause said diseased cementum and said diseased dentin to fracture;
   (e) irrigating the lesion during steps (c) and (d) with a fluid to remove fractured and fragmented plaque, calculus and fractured cementum and dentin;
   (f) removing said dental instrument;
   (g) inserting a curette into said lesion to remove remaining dislodged cementum, calculus and plaque; and
   (h) closing the lesion by applying pressure for a time sufficient to promote attachment of the gum to the tooth; and
   (i) wherein the dental instrument has a prong, and said probe and the instrument prong have the same included angle of between 119° to 121° between shank and tip portions thereof and are used in the treatment of the lower gums.

24. A method for treatment and control of periodontal disease and regeneration of periodontal tissues accomplished with the gum tissue remaining in place and connected between the teeth comprising the steps of:
   a. tracing the gum-tooth junction with a contoured probe to locate a periodontal lesion;
   b. inserting an instrument having a smooth nonabrasive exterior surface without a sharp edge capable of imparting energy to the contents of the lesion and its environs;
   c. applying energy with said instrument to dislodge and remove microbes, plaque, and calculus contained in said periodontal lesion;
   d. supplying sufficient energy with said instrument to cause disease affected cementum and disease affected dentin to fracture, cleave, and disintegrate from the tooth;
   e. supplying sufficient vibrational energy with said instrument to remove sufficient disease affected soft tissue to destroy and detach epithelium within said periodontal lesion and to produce bleeding;
   f. supplying sufficient vibrational energy with said instrument to fractionate, disintegrate and destroy microbes within said lesion and its environs;
   g. irrigating or flooding said periodontal lesion and environs during steps (c) and (d) with a fluid to enhance transmission of vibrating energy;
   h. irrigating or flooding said periodontal lesion and environs during steps (c) and (d) with a fluid to remove fractured and fragmented microbial debris, plaque, calculus, cementum and dentin;
   i. removing said instrument;
   j. inserting an instrument into said periodontal lesion to remove clotted blood and any remaining dislodged or free fractured and fragmented microbial debris, plaque, calculus, cementum, dentin, and soft tissue;
   k. allowing blood to reclot; and
   l. applying pressure of sufficient magnitude and duration to conform the gum to underlying hard structures, condense blood clot, and promote attachment of the surrounding tissue to the tooth, thereby enhancing said regeneration.

25. The method of claim 24, further comprising:
   reinserting said probe to isolate diseased dentin and cementum before proceeding with step(J), thereafter repeating steps (b) through (i) until reinsertion of the probe confirms all of said diseased cementum and dentin is removed, and
   scraping and removing soft tissue from the inside of said lesion with an instrument with sharpened edges.

26. The method of claim 24, wherein an antibiotic is administered in conjunction with step (a).

27. The method of claim 24, wherein a membrane is placed in the treated lesion between soft gum tissue wall and underlying bone and tooth root, and left during a healing stage.

28. A method of treatment of periodontal disease, its effects and regeneration of disease affected periodontal tissues comprising: leaving the gingival tissues in place and continuous around the teeth and connected to the teeth while detaching said gingival tissues from said teeth and other subjacent structures where access to disease affected tissue is needed for surgical manipulation, inserting a mechanical tool having a smooth nonabrasive exterior surface without a sharp edge into a periodontal lesion and energizing said tool to cause vibrating energy of sufficient intensity to be conducted into and released within the periodontal lesion to destroy, to at least prepare for removal or release of the disease producing agents and unwanted disease affected tissues from appropriate subjacent structures, to create appropriate physiological reactions, and to leave the various tissues forming the boundaries of said lesion in appropriate histological, biochemical, and microbiological condition to enhance regeneration of the periodontium, thereby enhancing regeneration of disease affected periodontal tissues.

29. A method of treatment of periodontal disease, its effects, and regeneration of disease affected periodontal tissues comprising: leaving the gingival tissues in place and continuous around the teeth and connected to the teeth while detaching said gingival tissues from said teeth and other subjacent structures where access to disease affected tissue is needed for surgical manipulation, inserting a mechanical tool having a smooth nonabrasive exterior surface without a sharp edge into a periodontal lesion and exciting said tool to cause vibrating energy of sufficient intensity to be conducted into and released within the periodontal lesions to destroy, and to at least prepare for removal of microbes associated with the lesion, thereby enhancing regeneration of disease affected periodontal tissues.

30. A method of treatment of periodontal disease, its effects, and regeneration of disease affected periodontal tissues comprising: leaving the gingival tissues in place and continuous around the teeth and connected to the teeth while detaching said gingival tissues from said teeth and other subjacent structures where access to disease affected tissue is needed for surgical manipulation, inserting a mechanical tool having a smooth nonabrasive exterior surface without a sharp edge into a periodontal lesion and exciting said tool to cause vibrating energy of sufficient intensity to be conducted into and released within the periodontal pocket or periodontal sulcus to destroy, disintegrate, and at least prepare for removal unwanted periodontal soft tissues, thereby enhancing regeneration of disease affected periodontal tissues.

31. A method of preparing a tooth root and adjacent periodontal structures for the generation of attachment of said adjacent periodontal structures to the tooth root surface from within a periodontal pocket or periodontal sulcus leaving the gingival tissues in place and continuous around the teeth and connected to the teeth but detached from the teeth and other subjacent structures where access to tissue is needed for surgical manipulation whereby a mechanical means of suitable proportions with a smooth nonabrasive exterior surface without a sharp edge is inserted into the periodontal lesion and conducting vibrating, energy of sufficient intensity into and released within the periodontal pocket or periodontal sulcus to cleave, fracture, and/or disintegrate from said tooth root surface any distorted tissue comprising said tooth root surface so that undistorted tissue comprises the tooth root surface and to at least prepare for removal of epithelium and immediately subjacent connective tissue from the periodontal structures adjacent to said root surface and also to create appropriate physiological reactions, and to leave the various tissues forming the boundaries of said pocket or sulcus in appropriate histological, biochemical, and microbiological condition to enhance joining and attaching of the adjacent hard and soft tissues related to said pocket or sulcus biologically, thereby enhancing regeneration of undistorted tissue.

32. A method of generating bone in a bone defect existing in the periodontal region of a tooth root and preparing a tooth root and adjacent periodontal structures for said generation of bone from within a periodontal pocket or periodontal sulcus, comprising leaving the gingival tissues in place and continuous around the teeth and connected to the teeth, but detached from the teeth and other subjacent structures where access to tissue is needed for surgical manipulation, inserting a tool having a smooth nonabrasive exterior surface without a sharp edge into the bone defect through a periodontal lesion or sulcus and through said tool applying vibrating energy of sufficient intensity into and released within said bone defect and said periodontal pocket or periodontal sulcus to cleave, fracture, and/or disintegrate from said tooth root surface any distorted tissue comprising said surface tooth root so that undistorted tissue comprises the surface tooth root and at least prepare for removal of soft tissue from the periodontal structures adjacent to said root surface, and at least prepare for removal all soft tissue from within said bone defect, to thereby release all soft tissue and periosteum from a band of suitable width at the periphery of said bone defect, to open intertrabecular spaces and make them continuous with said bone defect, to create appropriate physiological reactions, and to leave the various tissues forming the boundaries of said bone defect and related surgical access site in appropriate histological, biochemical, and microbiological condition to enhance the growth of bone tissue into said bone defect, thereby enhancing periodontal regeneration.

33. A method of stimulating the immune response of a host afflicted with a periodontal infection leaving the gingival tissues in place and continuous around the teeth and connected to the teeth where healthy but detached from the teeth and other subjacent structures where access to disease affected tissue is needed for surgical manipulation comprising: inserting a tool having a smooth nonabrasive exterior surface without a sharp edge into a periodontal lesion and conducting vibrating energy of sufficient intensity through said tool into and released within the periodontal lesion to destroy, to disintegrate, and to fractionate microbes within said lesion and surrounding tissues into relatively fine particles, to remove soft tissue lining the lesion and expose connective tissue elements, tissue fluids, and circulatory vessels, fluids, and cells to the relatively fine fractionated microbial particles created by the energy released within the lesion, whereby said particles then stimulate a host immune response, and enhancing regeneration of the connective tissue elements.

34. A method for treatment and control of periodontal disease and regeneration of periodontal tissues with the gum tissue remaining in place and connected between the teeth, comprising the steps of:
 (a) tracing the gum-tooth interface with a contoured probe to locate a periodontal lesion;
 (b) inserting a dental instrument with a smooth nonabrasive exterior surface without a sharp edge into said lesion;
 (c) applying vibrational energy with said dental instrument to remove plaque and calculus contained in said lesion and contacting the tooth;
 (d) contacting diseased cementum and diseased dentin with said dental instrument while applying sufficient vibrational energy with said dental instrument to cause said diseased cementum and said diseased dentin to fracture;
 (e) removing said dental instrument;
 (f) inserting a curette into said lesion to remove remaining dislodged cementum, dentin, calculus and plaque; and
 (g) closing the lesion by applying pressure for a time sufficient to promote attachment of the gum to the teeth, thereby enhancing regeneration of periodontal tissues.

35. A method for treatment and regeneration of periodontal tissues with the gum tissue remaining in place and connected between the teeth, comprising the steps of:
 (a) tracing the gum-tooth interface with a contoured probe to locate a periodontal lesion;
 (b) inserting a dental instrument with a smooth nonabrasive exterior surface without a sharp edge into said lesion;
 (c) applying vibrational energy to said dental instrument to remove plaque and calculus contained in said lesion;
 (d) contacting at least one of cementum, dentin, and bone with said dental instrument while applying sufficient vibrational energy with said dental instrument to cause said one of said cementum and dentin to fracture and soft tissue to disintegrate away from tooth and bone; thereby creating a surgical flap for management of at least regeneration of periodontal tissue which has an un-interrupted superficial surface subtending a number of teeth, which is dissected from the underlying bone and tooth root as required for surgical access but remains continuous between the teeth and from which at least an appropriate amount of soft tissue is removed from the internal aspect of to provide adequate flexibility through retraction and stretching for access to and assessment of subjacent structures;

(e) irrigating the lesion during steps (c) and (d) with a fluid to remove any fractured and fragmented plaque, calculus and fractured cementum and dentin;

(f) removing said dental instrument;

(g) inserting a curette into said lesion to remove remaining dislodged cementum, calculus, plaque, dentin and soft tissue; and (h) closing the lesion by applying pressure for a time sufficient to promote attachment of the gum surgical flap to the tooth, thereby enhancing regeneration of periodontal tissues.

* * * * *

UNITED STATES PATENT AND TRADEMARK OFFICE
CERTIFICATE OF CORRECTION

PATENT NO. : 5,188,531
DATED : February 23, 1993
INVENTOR(S) : Lloyd Von Sutfin

It is certified that error appears in the above-identified patent and that said Letters Patent is hereby corrected as shown below:

Title page, item [19], line 2, delete "Von";

Title page, item [76], delete "Von" and insert --V.--;

Title page, item [57], line 6, delete "prove" and insert --probe--;

line 11, delete "cauese" and insert --cause--;

Col. 3, line 56, delete "IT" and insert --It--;

line 59, before "different", delete "the";

Col. 4, line 55, after "lensions", insert --,--;

Col. 5, line 3, delete "detock" and insert --detach--;

Col. 7, line 10, insert --root-- after "for".

line 23, delete "insert";

Col. 8, line 34, after "tissue", insert --,--;

line 34, after "bacteria", insert --,--;

Col. 9, line 10, delete "Application" and insert --By application--;

UNITED STATES PATENT AND TRADEMARK OFFICE
CERTIFICATE OF CORRECTION

PATENT NO.  :  5,188,531
DATED       :  February 23, 1993
INVENTOR(S) :  Lloyd Von Sutfin It is certified that error appears in the above-identified patent and that said Letters Patent is hereby corrected as shown below:

Col. 10, line 12, delete "present" and insert --the--;

line 17, delete "omnidirectionally" and insert --omnidirectional--;

Col. 11, line 37, delete "p resent" and insert --present--;

line 46, delete "is";

line 47, delete ". A" and insert --, a--;

Col. 12, line 11, delete "into the";

Col. 14, line 23, delete "from bone".

Signed and Sealed this

Twenty-sixth Day of April, 1994

Attest:

BRUCE LEHMAN

*Attesting Officer*      *Commissioner of Patents and Trademarks*